(12) United States Patent  
Ogata et al.

(10) Patent No.: US 11,717,334 B2  
(45) Date of Patent: Aug. 8, 2023

(54) RADIOFREQUENCY GUIDEWIRE WITH CONTROLLED PLASMA GENERATION AND METHODS OF USE THEREOF

(71) Applicant: Asahi Medical Technologies, Inc., Pleasanton, CA (US)

(72) Inventors: Wayne Ogata, San Ramon, CA (US); Xiang Ian Gu, Foster City, CA (US); Steven Meyer, Oakland, CA (US); Osamu Katoh, Nagoya (JP)

(73) Assignee: ASAHI MEDICAL TECHNOLOGIES, INC., Pleasanton, CA (US)

( * ) Notice: Subject to any disclaimer, the term of this patent is extended or adjusted under 35 U.S.C. 154(b) by 412 days.

(21) Appl. No.: 15/047,246

(22) Filed: Feb. 18, 2016

(65) Prior Publication Data

US 2016/0235463 A1    Aug. 18, 2016

Related U.S. Application Data

(60) Provisional application No. 62/117,828, filed on Feb. 18, 2015.

(51) Int. Cl.
*A61B 18/04*    (2006.01)
*A61B 17/22*    (2006.01)
(Continued)

(52) U.S. Cl.
CPC ............ *A61B 18/042* (2013.01); *A61B 17/22* (2013.01); *A61B 18/1482* (2013.01); (Continued)

(58) Field of Classification Search
CPC .............. A61B 18/042; A61B 18/1482; A61B 18/1492; A61B 18/04–18; A61B 17/22; (Continued)

(56) References Cited

U.S. PATENT DOCUMENTS

| 5,047,026 A | 9/1991 | Rydell |
| 5,716,389 A | 2/1998 | Walinsky et al. |

(Continued)

FOREIGN PATENT DOCUMENTS

| JP | 2004-505663 A | 5/2004 |
| JP | 2010-540198 A | 12/2010 |

(Continued)

OTHER PUBLICATIONS

International Search Report for corresponding International Patent Application No. PCT/US2016/18482 (dated Jun. 13, 2016), pp. 1-10.

(Continued)

*Primary Examiner* — Eun Hwa Kim  
*Assistant Examiner* — Catherine Premraj  
(74) *Attorney, Agent, or Firm* — Troutman Pepper Hamilton Sanders LLP (Rochester)

(57) ABSTRACT

A radiofrequency guidewire includes a core wire configured to be coupled to a radiofrequency generator. The core wire includes a proximal end and a distal end with respect to the radiofrequency generator. A tip structure is coupled to the core wire proximate the distal end. The tip structure includes one or more edge surfaces. The one or more edge surfaces provide an area of reduced curvature radius on the tip structure. The area of reduced curvature radius generates a higher electric field than other areas of the tip structure during a delivery of radiofrequency energy on the tip structure. A method of ablating an occlusion utilizing the radiofrequency guidewire is also disclosed.

36 Claims, 9 Drawing Sheets

(51) Int. Cl.
*A61B 18/14* (2006.01)
*A61B 18/00* (2006.01)

(52) U.S. Cl.
CPC ............ *A61B 18/1492* (2013.01); *A61B 2017/22042* (2013.01); *A61B 2017/22094* (2013.01); *A61B 2018/00577* (2013.01); *A61B 2018/00755* (2013.01); *A61B 2018/00785* (2013.01); *A61B 2018/141* (2013.01)

(58) Field of Classification Search
CPC ........... A61B 2017/22042; A61B 2017/22094; A61B 2018/00577; A61B 2018/00755; A61B 2018/00785; A61B 2018/141; A61M 25/005; A61M 25/0068
See application file for complete search history.

(56) References Cited

U.S. PATENT DOCUMENTS

| | | | |
|---|---|---|---|
| 6,162,221 A | 12/2000 | Ouchi | |
| 6,950,710 B2 * | 9/2005 | Shirakawa | A61N 1/05 607/122 |
| 7,070,596 B1 * | 7/2006 | Woloszko | A61B 18/1482 606/41 |
| 2001/0012934 A1 * | 8/2001 | Chandrasekaran | A61B 18/1492 606/41 |
| 2004/0181219 A1 | 9/2004 | Goble et al. | |
| 2006/0084964 A1 * | 4/2006 | Knudson | A61M 25/0122 606/41 |
| 2006/0282016 A1 * | 12/2006 | Cornelius | C08L 83/04 600/585 |
| 2009/0093802 A1 | 4/2009 | Kulesa et al. | |
| 2010/0191151 A1 | 7/2010 | Kwak | |
| 2011/0087211 A1 * | 4/2011 | Kulesa | A61B 18/1492 606/34 |
| 2011/0118735 A1 * | 5/2011 | Abou-Marie | A61B 18/1492 606/45 |
| 2013/0103021 A1 * | 4/2013 | Germain | A61B 17/320016 606/33 |
| 2013/0131513 A1 | 5/2013 | Katoh et al. | |

FOREIGN PATENT DOCUMENTS

| | | |
|---|---|---|
| JP | 2011-518615 A | 6/2011 |
| JP | 2013-523285 A | 6/2013 |
| JP | 2014-531935 A | 6/2017 |
| WO | 2009061860 | 5/2009 |

OTHER PUBLICATIONS

European Search Report for corresponding European Patent Application No. 16753064.1, dated Jul. 16, 2018, pp. 1-11.
Office Action for corresponding India Application No. 201747032150, dated May 5, 2021.
Office Action for corresponding Japan Application No. 2017-543729, dated May 10, 2021.
Office Action for corresponding China Application No. 2016800127211, dated Mar. 23, 2021.
Office Action for Chinese Patent Application No. 201680012721.1, dated Oct. 13, 2021.
Canada Intellectual Property Office, Examiner's Requisition, dated Feb. 3, 2022.
JP Office Action dated Mar. 8, 2023, for Japan National Application No. 2017-543729.
Canadian Intellectual Property Office, Second Examiner's Requisition, dated Jan. 5, 2023 re Application No. 2,976,386.

* cited by examiner

RADIOFREQUENCY GUIDEWIRE WITH CONTROLLED PLASMA GENERATION AND METHODS OF USE THEREOF

This application claims benefit of U.S. Provisional Patent Application Ser. No. 62/117,828, filed on Feb. 18, 2015, which is hereby incorporated by reference in its entirety.

FIELD

This technology generally relates to radiofrequency guidewires and methods, and more particularly to radiofrequency guidewires with controlled plasma generation and methods thereof.

BACKGROUND

Chronic total occlusion (CTO) is the complete blockage of a vessel and may have serious consequences if not treated in a timely fashion. The blockage could be due to atheromatous plaque or old thrombus.

One of the common procedures for treating CTOs of the coronary arteries is percutaneous transluminal coronary angioplasty (PTCA). During a PTCA procedure, a small incision is typically made in the groin. A guiding catheter over a guidewire is introduced into the femoral artery and advanced to the occlusion. At times, with gentle maneuvering, the guidewire is able to cross the occlusion. A balloon-tipped angioplasty catheter is then advanced over the guidewire to the occlusion. The balloon is inflated, separating or fracturing the atheroma. Often times, a stent is subsequently or simultaneously deployed.

Some of the common steps involved in the PTCA procedure for CTOs are the simultaneous injection of a contrast agent in the contra-lateral vessel, securing backup force or stabilization for a guidewire (which could invoke additional personnel to handle the catheter), puncturing the plaque, or drilling or rotating the guidewire to push it through the dense plaque by way of example only. Because of the stiff resistance sometimes offered by dense plaque, one could be forced to use stiff wires. Occasionally, the wires could puncture the vessel wall calling for remedial measures.

The most common percutaneous coronary intervention (PCI) failure mode for CTOs is inability to successfully pass a guidewire across the lesion into the true lumen of the distal vessel. To date, there is no consensus on how best to treat CTOs after attempts with conventional guidewires have failed. Different strategies for CTOs have been developed including the side branch technique, the parallel wire technique, and the IVUS guided technique. Mechanical and energy based devices have also been proposed for passing guidewires through hard calcified occlusions, such as mechanical cutting or oscillation and laser or ultrasound or radiofrequency (RF) energy ablation. These devices work by locally applying energy (typically in the form of heat) at the tip of the guidewire or catheter device in order to create a channel and hopefully enter the distal true lumen.

RF energy is widely used to coagulate, cut, or ablate tissue. In both monopolar and bipolar modalities, conductive electrodes contact the tissue to be treated. In the monopolar mode, the active electrode is placed in contact with the tissue to be treated and a return electrode with a large surface area is located on the patient at a distance from the active electrode. In the bipolar mode, the active and return electrodes are in close proximity to each other bracketing the tissue to be treated. Sometimes an array of electrodes is used to provide better control over the depth of penetration of the RF field and hence control over the temperatures to which the tissue is heated.

There are many disadvantages with both monopolar and bipolar modalities. For example, in the monopolar arrangement, because of the large physical separation between the electrodes there are frequent reports of local burning at the electrode sites. This would clearly be undesirable where one of the electrodes will be inside a blood vessel. The other serious issue is the likelihood of forming blood clots. The tissue that is in contact with the electrodes can be coagulated or ablated. In the case of the electrodes being present inside a blood vessel, the formation of dangerous blood clots would obviously be undesirable.

Plasma-based tissue ablation has also been widely used in electrosurgical applications. Laser or RF pulses can ionize molecules to form small sized plasma that ablates tissue with minimum heat transfer to surrounding area, leading to very limited collateral thermal damage to the surrounding tissue. Conventional approaches utilize thermal effects caused by continuous Joule heating to remove tissue. By contrast, in pulsed plasma-mediated RF tissue ablation, a strong electrical field interacts with the medium (such as saline and/or blood) and tissue to excite electrolytes and molecules. When a threshold is reached, the molecules are ionized and fragmented, resulting in an ionized plasma field that effectively converts the high electron energy for the removal of tissue. Plasma-mediated RF ablations have noticeable advantages, for example, thermal effects are normally insignificant due to the very short pulse duration of RF energy application. Furthermore, plasma-mediated RF ablation can remove a wide range of tissues including hard tissues, while conventional thermal ablations may be less effective to ablate high-impedance tissues due to less electrical conductivity. The control of plasma ablation, however, may be limited.

In an attempt to overcome the issues described above, various device and electrode configurations have been developed to use RF electrodes on a single catheter in a bipolar electrode assembly at the distal tip structure of a catheter that is in contact with the occlusion to cross a lesion. The application of RF energy ablates the occlusion and renders the occlusion susceptible for the guidewire to penetrate. This method has the drawback that careful tracking of the occlusion and the ablation process is necessary to avoid trauma to the vessel walls or healthy tissue, since the possibility of short-circuiting of current through healthy tissue instead of the occlusion is high. Multielectrode arrays have been proposed to remedy this problem. Such devices, however, require a channel to be pre-created through the occlusion so that the device can be passed through a guidewire traversing this channel, which is not always easy. The need for a guidance system, potential for healthy tissue to be ablated, and complexity (and hence cost) of the device are drawbacks to using radiofrequency energy.

One major problem with the existing devices is the potential for the ablation energy to damage the walls of the vasculature, in the absence of a mechanism to track the orientation and position of the energy delivery member. Several devices have been developed that address the issue of tracking and steering of the energy delivery element, such as a magnetic steering and guidance system to direct an ablation device that delivers RF energy at the tip in a unipolar configuration where the return electrode is placed externally in contact with the body or in a bipolar configuration where the return electrode is a ring surrounding the central wire electrode. Such a guidance system creates complexity and high costs.

However, none of these alternate strategies have provided satisfactory results for the most challenging of CTOs. In the case of hard calcified occlusions, the revascularization procedure can be tedious and time consuming. Therefore, there is a need for improved methods of ablating or disrupting the occlusive material using radiofrequency energy that are safe, efficacious, and fast, without the drawbacks of the current techniques, particularly the difficulties in directing the radiofrequency energy to the occlusion site.

SUMMARY

A radiofrequency guidewire includes a core wire configured to be coupled to a radiofrequency generator. The core wire includes a proximal end and a distal end with respect to the radiofrequency generator. A tip structure is coupled to the core wire proximate the distal end. The tip structure includes one or more edge surfaces. The one or more edge surfaces provide an area of reduced curvature radius on the tip structure. The area of reduced curvature radius generates a higher electric field than other areas of the tip structure during a delivery of radiofrequency energy on the tip structure.

A method for ablating an occlusion includes delivering a guidewire to the occlusion. The guidewire includes a core wire configured to be coupled to a radiofrequency generator. The core wire includes a proximal end and a distal end with respect to the radiofrequency generator. A tip structure is coupled to the core wire proximate the distal end. The tip structure includes one or more edge surfaces that provide an area of reduced curvature radius on the tip structure. An opposing electrode is positioned proximate the tip structure. Radiofrequency energy is delivered through the guidewire from the radiofrequency generator. An electrical field is generated proximate the tip structure with the electrical field strongest at the one or more edge surfaces to generate a plasma at the one or more edge surfaces to ablate the occlusion.

The radiofrequency guidewire and methods of the present technology advantageously deliver radiofrequency energy to an occlusion for a more controlled generation of plasma. This provides for increased effectiveness of radiofrequency energy for dissipated occlusions, as well as increased safety, including the use of lower voltage levels and lower energy levels. Additionally, the direction of energy away from the insulating material allows for the use of thinner, more flexible materials, providing better access to occlusions.

BRIEF DESCRIPTION OF THE DRAWINGS

4A-4D are schematics of exemplary distal tip structures that may be utilized with the guidewire of this technology.

DETAILED DESCRIPTION

Figure 1:
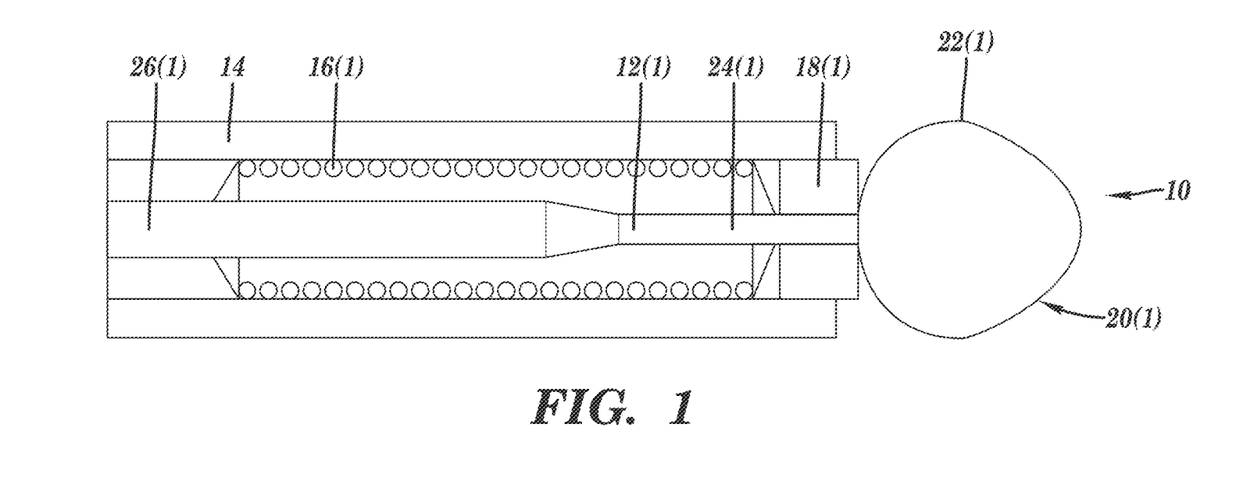
FIG. 1 is a side, partial cross-sectional view of an exemplary radiofrequency guidewire.

An exemplary radiofrequency guidewire 10 of the present technology is illustrated in FIG. 1. The radiofrequency guidewire 10 includes a core wire 12(1), an outer layer 14, a spring coil 16(1), a collar 18(1), and a distal tip structure 20(1) with at least one edge surface 22(1), although the radiofrequency guidewire 10 may include other types and/or numbers of other components or elements in other configurations. Accordingly, this exemplary technology provides a number of advantages including providing a radiofrequency guidewire that directs the generation of plasma towards an opposing electrode and along an outer edge of the distal tip structure to avoid exposing the plasma to vulnerable insulation material near the base of the distal tip structure. Further, directing the plasma generation to the outer edges allows for creation of a broader channel within the occlusion. The presence of a small curvature radius on the distal tip structure creates an area with a stronger electric field (relative to other areas on the guidewire) and thus will initiate plasma formation at that site and constrain the plasma to the distal tip structure.

Referring more specifically to FIG. 1, the radiofrequency guidewire 10 includes the core wire 12(1), which extends along the axial length of the radiofrequency guidewire 10. The core wire 12(1) is constructed of a conductive material, such as stainless steel, copper, Nitinol, Elgiloy, platinum, MP35N silver, tantalum, titanium, tungsten, or any combination thereof, although other conductive materials in other combinations may be utilized. The core wire 12(1) is coupled to a radiofrequency generator (not shown) in order to provide radiofrequency energy through the core wire 12(1).

In this example, the core wire 12(1) includes a distal section 24(1) located near the distal tip structure 20(1) and a proximal section 26(1) coupled to the distal section 24(1). In this example, the distal section 24(1) has a tapered diameter from the proximal section 26(1) of the core wire 12(1), although the core wire 12(1) may have other numbers of sections in other configurations. The distal section 24(1) of the core wire 12(1) has a diameter of less than 0.004 inches at the distal end, although other sizes for the distal section 24(1) may be utilized. The proximal section 26(1) is approximately 0.012 inches in diameter, although other diameters may be utilized for the proximal section 26(1).

Figure 2:
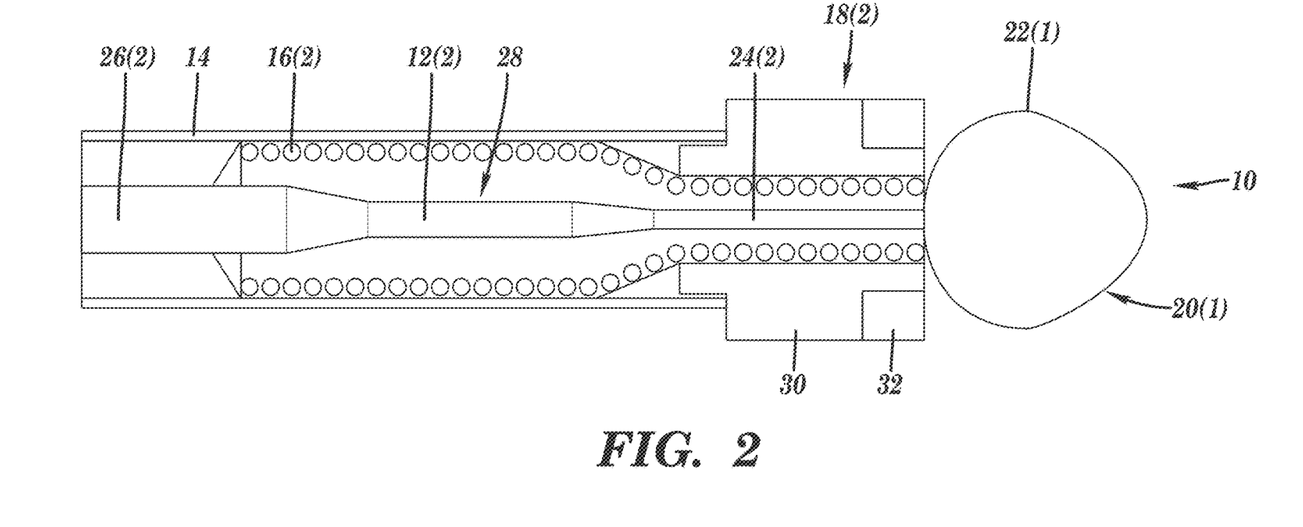
FIG. 2 is a side, partial cross-sectional view of another example of the radiofrequency guidewire.

In another example, referring now to FIG. 2, the radiofrequency guidewire 10 includes a core wire 12(2) having a distal section 24(2), a proximal section 26(2), and a middle section 28, although the core wire 12(2) may have other numbers and types of sections. The core wire 12(2) decreases in diameter from the proximal section 26(2) to the middle section 28. The core wire 12(2) further decreases in diameter from the middle section 28 to the distal section 24(2), although other configurations may be utilized. Alternatively, the core wire 12(1) or 12(2) may be in the form of a hypotube or drawn filled tubing.

Referring again to FIG. 1, the outer layer 14 extends along the axial length of the core wire 12(1) to provide both thermal and electrical insulation for the core wire 12(1). The outer layer 14 is constructed of an insulation material with high dielectric strength, such as polymide, PTFE, parylene, or PFA, although other types and/or numbers of other materials with high dielectric strength may be utilized. In one example, the outer layer 14 is a polyimide material with a dielectric strength of approximately 7200V/mil and has a wall thickness between approximately 0.005 inches and 0.0005 inches, although the outer layer 14 may have other parameters. Polyimide may be utilized for the outer layer 14 for its high tensile strength, which aids in imparting a strong axial force for the radiofrequency guidewire 10(1).

The spring coil 16(1) is utilized near the distal tip structure 20(1) of the radiofrequency guidewire 10. The spring coil 16(1) adds flexibility to the radiofrequency guidewire 10 to allow for delivery in tortuous anatomy. The spring coil 16(1) also serves as a parallel pathway for current sent from an RF generator through the core wire 12(1) to lower the thermal condition in the distal section 24(1) of the radiofrequency guidewire 10. The spring coil 16(1) essentially serves as a resistor in parallel with the core wire 12(1) and diverts at least some of the power, and therefore heat, away from the core wire 12(1).

The core wire 12(1), by way of example, may have several tapers along the axial length, which would essentially serve as additional resistors in series with the parallel combination of the core wire 12(1) and the spring coil 16(1). Lowering the thermal condition along certain pathways along the radiofrequency guidewire 10, for example the spring coil 16(1), allows for the use of less demanding materials (lower melt temperature, lower dielectric strength, etc.) for the outer layer 14, including thinner walls and more flexible materials. The spring coil 16(1) may have a length of approximately 80 mm, although spring coils having other lengths may be utilized. In another example, as illustrated in FIG. 2, a spring coil 16(2) that has a tapered configuration to extend further into the distal end of the radiofrequency guidewire 10 may be utilized, although spring coils with other configurations may be employed.

Referring again to FIG. 1, the collar 18(1) is located near the distal end of the core wire 12(1) to provide further thermal and/or electrical insulation near the distal tip structure 20(1). The collar 18(1) may be constructed of a high dielectric strength material and/or a material with a high melting temperature, such as PTFE, PFA, polymide, ceramic, or various metals or alloy by way of example only.

Referring now to FIG. 2, in another example, a collar 18(2) is utilized. The collar 18(2) includes a first collar section 30 and a second collar section 32, by way of example only. In this example, the first collar section 30 is constructed of a single material and is approximately 10 mm in length with a width that extends beyond the width of the outer layer 14 of the radiofrequency guidewire 10, although the first collar section 30 may have other configurations. The second collar section 32 is located at the distal end of the radiofrequency guidewire 10. In this example, the second collar section 32 extends approximately 0.25 mm in length and is constructed of a material with a higher melting temperature than the first collar section 30, although other configurations and materials may be utilized.

Figure 3A:
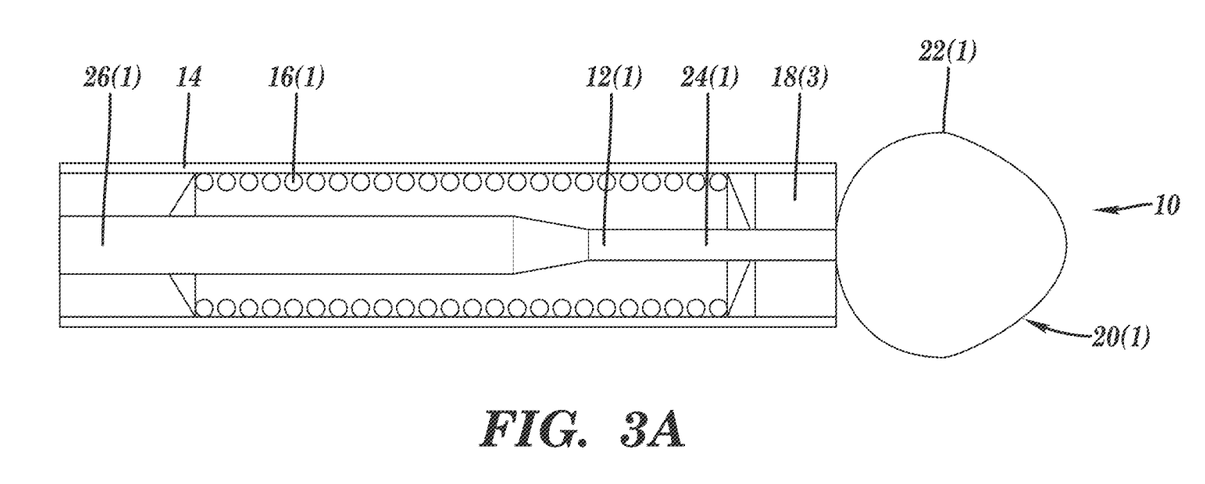
FIGS. 3A-3D are side, partial cross-sectional views of additional examples of the radiofrequency guidewires with different exemplary collar structures arranged proximate the distal tip structure.
Figure 3B:
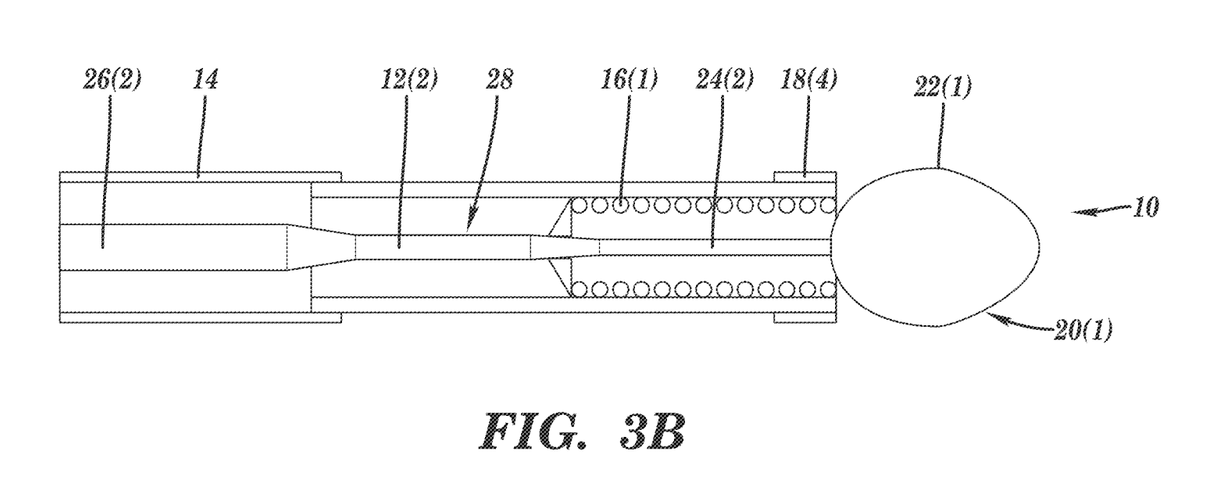

Referring again to FIG. 1, in this example, the collar 18(1) is located partially enclosed within the outer layer 14. The collar 18(1) has a length of approximately 0.25 mm to 0.50 mm, although the collar 18(1) may have other dimensions. In another example, the radiofrequency guidewire 10 includes a collar 18(3) that is entirely enclosed within the outer layer 14, as illustrated in FIG. 3A. The collar 18(3) has a length of approximately 0.25 mm to 0.50 mm, although the collar 18(3) may have other dimensions. In yet another example, the radiofrequency guidewire 10 includes a collar 18(4) that is positioned outside the outer layer 14, as illustrated in FIG. 3B. The collar 18(4) has a length of approximately 0.25 mm to 0.50 mm, although the collar 18(4) may have other dimensions.

Figure 3C:
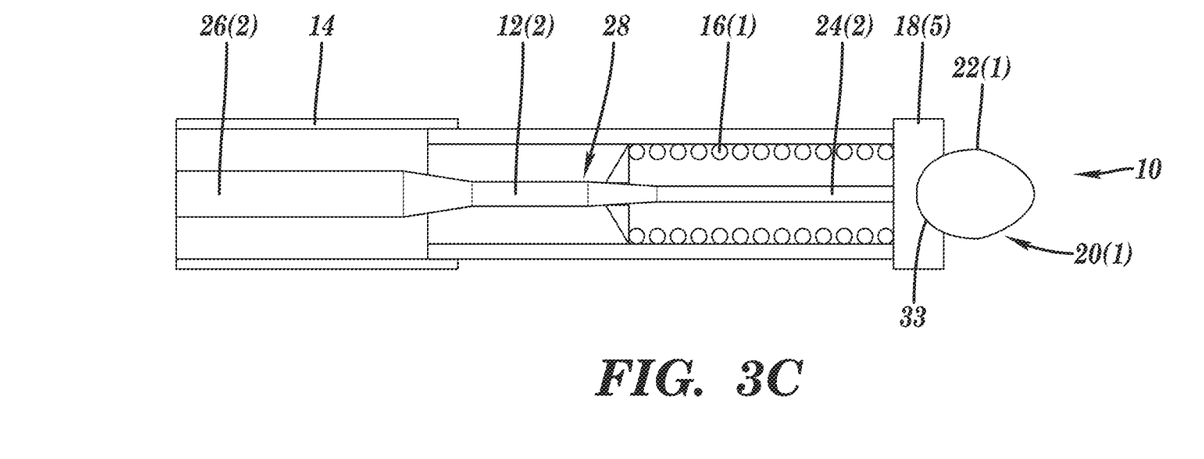

Alternatively, the radiofrequency guidewire 10 includes a collar 18(5) with a concave surface 33 configured such that the distal tip structure 20(1) is recessed within the collar 18(5), as illustrated in FIG. 3C, by way of example. During the initial stages of plasma formation, a vapor bubble is created around the distal tip structure. 20(1). The concave surface 33 of the collar 18(5) impedes backwards propagation of the vapor bubbles (including its accompanying shockwaves) and encourages plasma formation in the forward direction, i.e., in the direction away from the core wire 12(2) in this example.

Figure 3D:
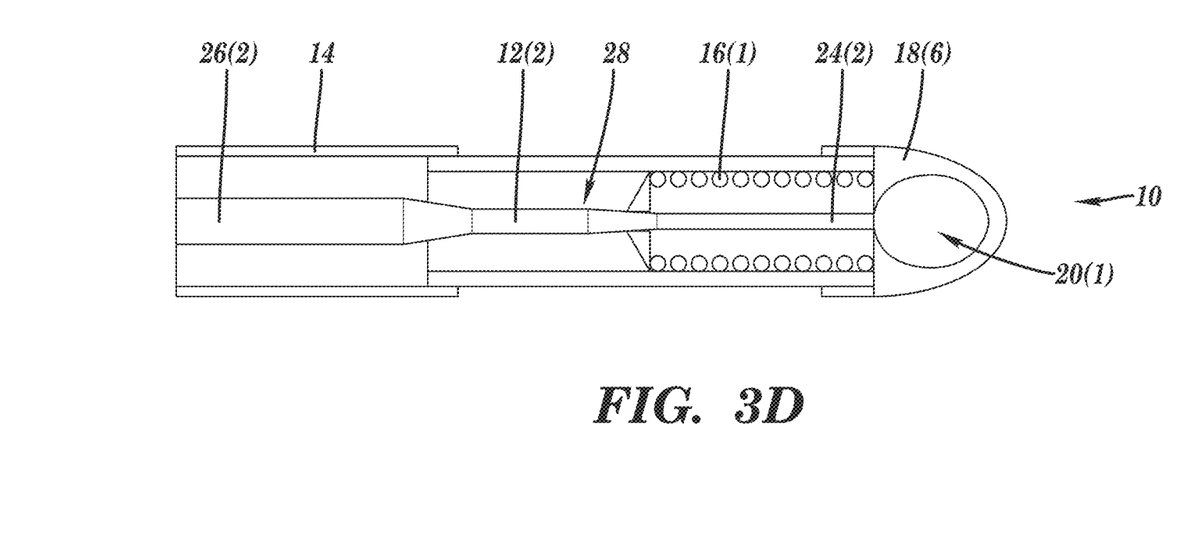

In yet another example, as illustrated in FIG. 3D, the radiofrequency guidewire 10 includes a collar 18(6) that encapsulates the distal tip structure 20(1) within a dielectric barrier, such as a ceramic material, although other dielectric materials may be utilized. In this example, a dielectric barrier-discharge generates plasma on and around the surface of the collar 18(6)

Referring again to FIG. 1, the distal tip structure 20(1) is located at the distal end of the core wire 12(1), opposite the radiofrequency generator (not shown). The distal tip structure 20(1) is in electrical communication with the core wire 12(1). The distal tip structure 20(1) serves as an electrode for delivering energy generated by a radiofrequency generator coupled to the core wire 12(1) for generating plasma at an occlusion site. The distal 20(1) tip is constructed of any suitable conductive material with a high melting temperature, such as stainless steel, titanium, tantalum, or tungsten, by way of example only.

Figure 4A:
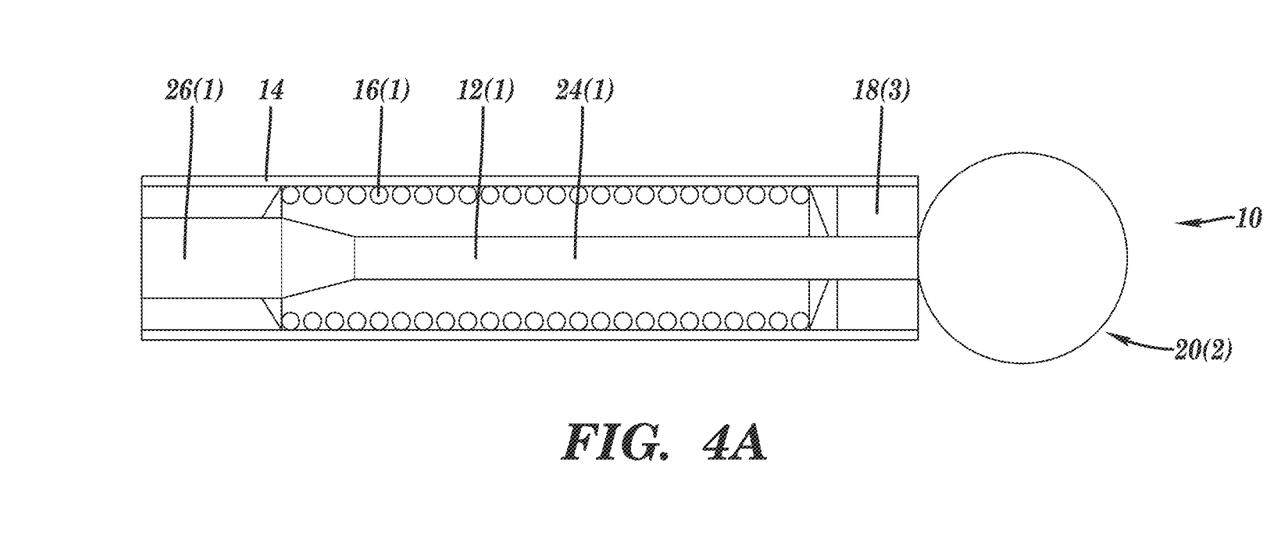

The distal tip structure 20(1) includes the edge surface 22(1) that provides a sharp area that is configured to provide a point of strongest electric field based on energy delivered from the radiofrequency generator to generate plasma at that location, although other numbers of edge surfaces may be utilized in other locations on the distal tip structure 20(1). Although the point of strongest electric field is generally located on the outer edge of the distal tip structure 20(1), it can be located anywhere along the length of the radiofrequency guidewire 10 where plasma is desired. For example, if the plasma were to be generated at a location proximal to the distal tip structure 20(1), the distal tip structure 20(1) would be insulated so that the plasma would form at the proximal location rather than the distal tip structure 20(1). The sharpness or edge radius of the curvature of the edge surface 22(1) may be configured dependent on the application. For example, the edge surface 22(1) may have a sharper angle (or smaller edge radius of curvature) to create a stronger electrical field in more difficult lesions with high impedance. Alternatively, a distal tip structure 20(2) that is a ball tip without any sharp edges, as illustrated in FIG. 4A may be utilized. The distal tip structure 20(2) provides uniform generation of plasma around the distal tip structure 20(2).

Figure 4B:
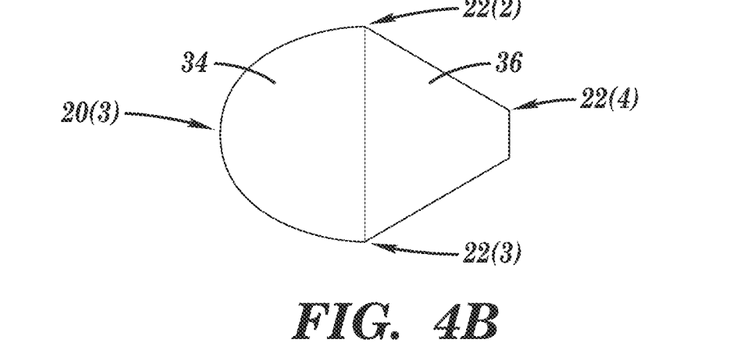
Figure 4C:
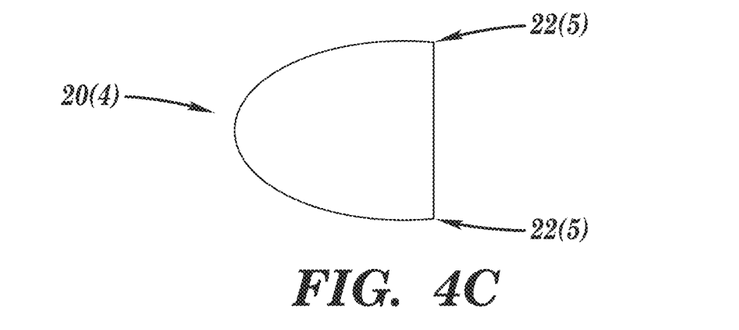
Figure 4D:
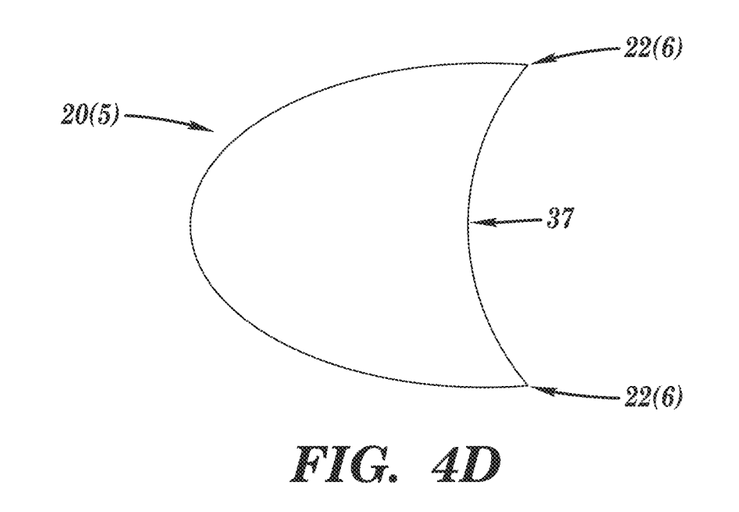

Referring now to FIGS. 4B-4D, various examples of distal tip structures 20(3)-20(5) that may be utilized with the radiofrequency guidewire 10 of the present technology are illustrated. In one example, as illustrated in FIG. 4B, the distal tip structure 20(3) includes a base 34 having a rounded configuration and a tapered section 36 extending from the base 34. The tapered section 36 includes sharp outer edges 22(2) and 22(3) extending from the rounded base 34 at approximately 45 degree angles. The tapered section 36 of the distal tip structure 20(3) also has an edge surface 22(4)

at the distal end, although other edge surfaces may be located at other locations on the distal tip structure 20(3) to direct plasma generation. In this example, the ratio of a length of the base 34 to a length of the tapered section 36 is greater than 50% such that plasma is generated away from the insulated collar, although other configurations may be utilized.

In another example, as illustrated in FIG. 4C, a distal tip structure 20(4) having a flat front edge that forms edge surfaces 22(5) on the outer edges may be utilized. In yet another example, a distal tip structure 20(5) with a concave front surface 37 to provide edges surfaces 22(6) at the outer edges may be employed as illustrated in FIG. 4D. The examples are configured to generate plasma at the outer edges. The sharper angles in these figures would allow more efficient formation of plasma at a lower voltage and energy input. Although some examples of distal tip structures are illustrated, the edge surfaces on the distal tip structure may be located anywhere along the distal tip structure to direct the generation of plasm, i.e., to create an area with a strongest electrical field, depending on the application.

An exemplary operation of the radiofrequency guidewire 10 will now be described with reference to FIGS. 1-8. The operation of radiofrequency guidewire 10 with the various configurations described above is the same except as illustrated and described herein. In operation, in this example, the radiofrequency guidewire 10 is directed toward an occlusion for treatment. Although the disclosure is generally directed to use of the radiofrequency guidewire in blood vessels, it can similarly be applied to areas of the body outside the blood vessels such as within various ducts (renal, bile, etc.) as well as on various tissues or organs of the body, such as tissue a prostate gland, a tumor, or a cardiac tissue, by way of example only. In such cases, the use of larger radiofrequency catheters may be warranted.

In one example, two radiofrequency guidewires 10 may be positioned near the occlusion using and antegrade and retrograde approach as described in U.S. Pat. No. 7,918,859, the disclosure of which is hereby incorporated by reference herein in its entirety, to provide opposite poles for the delivery of radiofrequency energy to the occlusion. Alternatively, a single radiofrequency guidewire 10 of the present technology may be delivered to the occlusion site and utilized with a second electrode located elsewhere in or on the patient's body, such as in the form of a skin patch. In yet another embodiment, two radiofrequency guidewires 10 may be brought into proximity of the occlusion from the same direction, although the radiofrequency guidewire 10 may be utilized with other devices in other applications using an antegrade/retrograde approach or delivered from the same direction.

Conventional mechanical guidewires typically have an atraumatic distal tip structure and rely primarily on axial force to push through and navigate an occlusion. This often leads to deflection of the atraumatic tip away from its intended course depending on the composition of the occlusion. Unlike conventional guidewires, the radiofrequency guidewire 10 of the present technology may have a relatively sharp distal tip structure 20(1) having edge surfaces 22(1), by way of example, as it relies on the assistance of the plasma that is formed locally between the two electrodes to "etch" its way through an occlusion, avoiding the axial forces that may result in deflection of the distal tip structure 20(1) away from its intended course. This approach is less dependent on the composition of the occlusion and requires less axial force. The spring coil 16(1) provides added flexibility to direct the radiofrequency guidewire 10 through tortuous anatomy.

Next, radiofrequency energy is delivered through the radiofrequency guidewire 10 by a radiofrequency generator. The radiofrequency energy is directed from one electrode to another. The electric field generated is highest at the edge surface 22(1) located on the distal tip structure 20(1), although other edge surfaces may be utilized as described above to generate the highest electric field in other areas about the distal tip structure. Thus, plasma generation is directed to those areas, such that plasma generation is controlled by the configuration of the distal tip structure 20(1) utilized.

By way of example, using a distal tip structure such as the distal tip structure 20(3) illustrated in FIG. 4B, by way of example, having the edge surface 22(4) located at the distal end of the distal tip structure 20(3) serves to generate plasma in that area. Alternatively, a distal tip structure such as the distal tip structure 20(4) illustrated in FIG. 4C, by way of example, with the edge surfaces 22(5) located at the outer edges of the distal tip structure 20(4) will direct plasma generation near those outer edges.

Figure 5A:
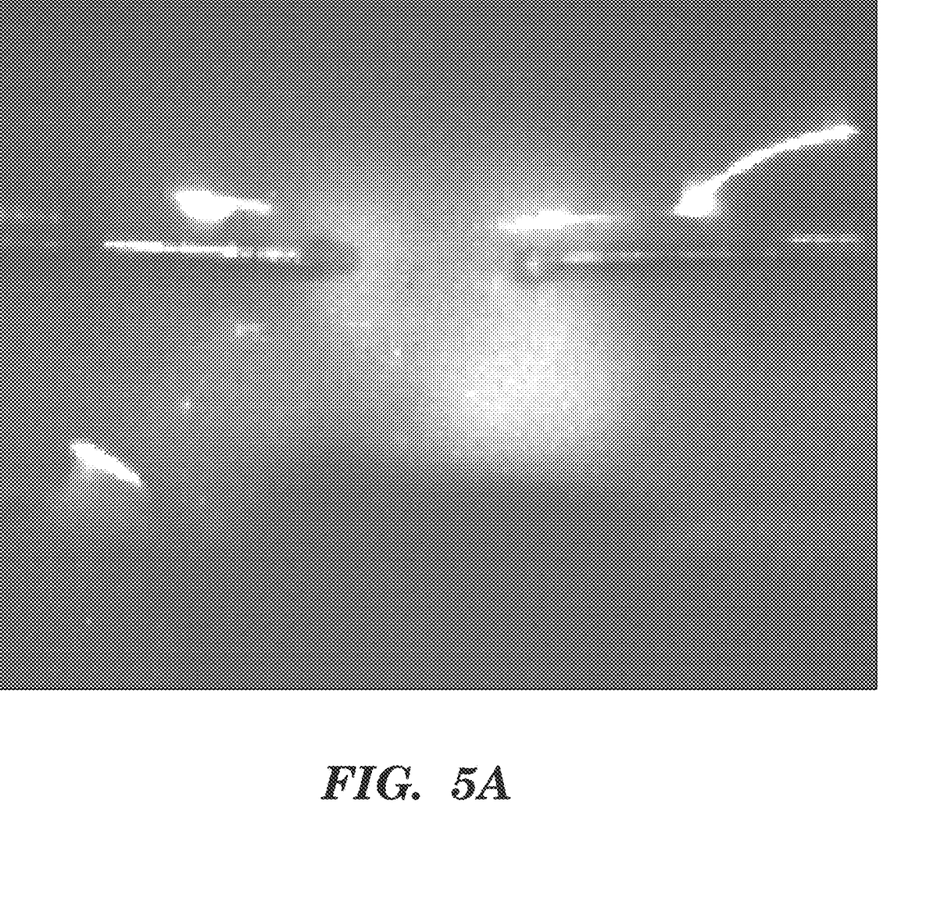
FIGS. 5A and 5B show images obtained using a high speed camera showing plasma generation for a guidewire of the present invention with a tapered distal tip structure having an edge surface (left) and with a ball tip (right).
Figure 5B:
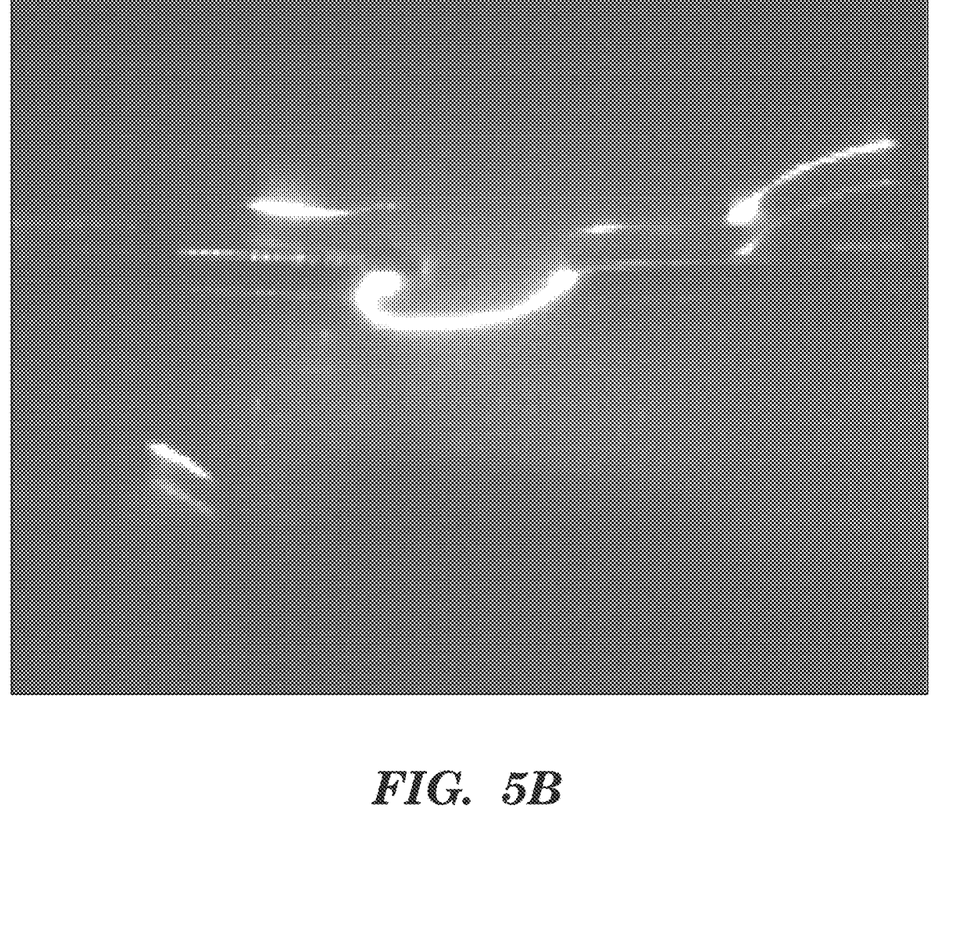

Referring to FIGS. 5A and 5B, a radiofrequency guidewire 10 of the present technology with the cone-shaped distal tip structure having at least one edge surface is shown on the left, and a radiofrequency guidewire 10 with the ball tip 20(2), as shown in FIG. 4A, is shown on the right. As shown in FIGS. 5A and 5B, the tapered distal tip structure 20(3) initiates the plasma on the outer edge of the tapered distal tip structure 20(3) (which has the strongest electric field) and directs the spark towards the ball tip 20(2) for a more controlled plasma generation.

Referring again to FIG. 1, modifying the configuration of the distal tip structure 20(1) allows customization or varying the energy delivery based on the tissue. By way of example, a higher impedance material such as calcium may require a different configuration (for example sharper angles) than a lower impedance material. Additionally, a small edge radius of curvature on the electrode may allow use of a lower energy input and more efficient delivery of energy.

Figure 6A:
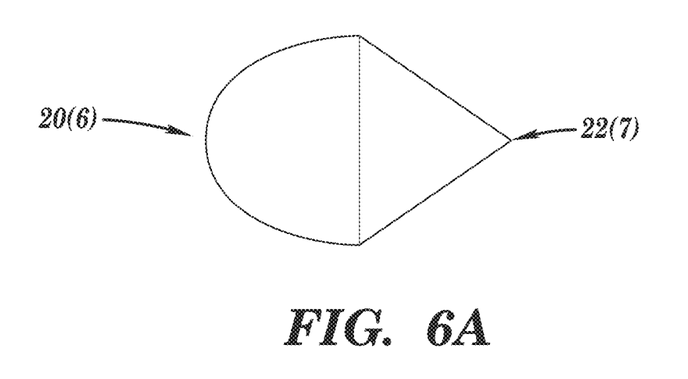
FIGS. 6A and 6B are diagrams of an example of alterations of a distal tip structure to generate variable plasma generation.
Figure 6B:
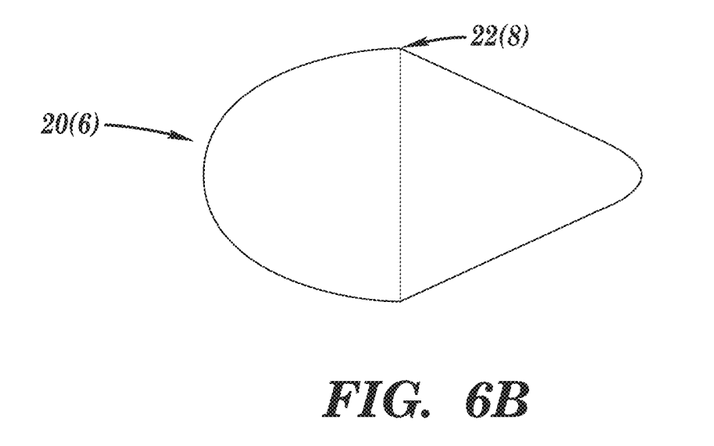

In another embodiment, as illustrated in FIGS. 6A and 6B the configuration of the distal tip structure 20(6) may be dynamically altered during operation of the radiofrequency generator to allow for variable plasma generation. FIG. 6A shows the distal tip structure 20(6) with an edge surface 22(7) located at the most distal point. During initial operation, the electrical field is highest at the apex (the edge surface 22(7)) on the tip, resulting in plasma generation in that area. After sputtering, i.e., deposition and removal of particles near the tip, as shown in FIG. 6B, the sharpest edge surfaces 22(8) are now located at the outer edges. The plasma generation will now occur at the outer edges 22(8). Although one dynamic change in plasma generation is described, the plasma generation could by dynamically altered in other manners.

Figure 7:
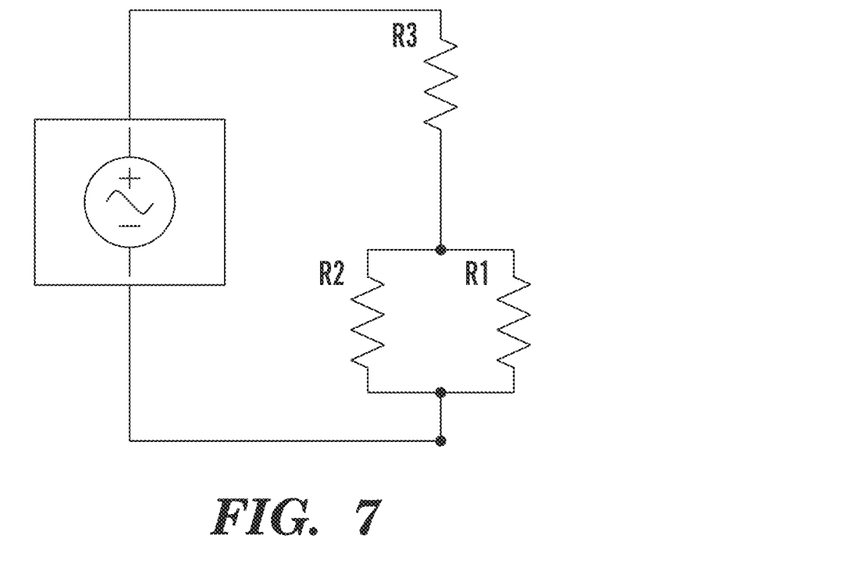
FIG. 7 is a simplified electrical schematic representing the radiofrequency guidewire shown in FIG. 4A.

FIG. 7 is an electrical representation of the guidewire illustrated in FIG. 4A. R3 is the resistance imposed by the proximal section 26(1) of the core wire 12(1) (at least partially due to skin effects). R1 is the resistance imposed by the tapered distal section 24(1) of the core wire 12(1) and R2 is the resistance imposed by the spring coil 16(1). By placing the spring coil 16(1) around the distal section 24(1) of the core wire 12(1), this can be viewed as placing a resistor (R2) in parallel with R1 and this parallel circuit combination can be viewed as being in series with the proximal section 26(1) of the core wire 12(1) R3. Thus, by adding R2 across R1, the parallel combination resistance drops below that of R1 alone. As R2 gets smaller, the parallel combination gets smaller and the voltage across R1 gets smaller. By adjusting R2 and R1, the parallel path exposed to the larger power dissipation and consequently heat may be adjusted.

The core wire 12(1) may have several tapers along its length, which would serve essentially as additional resistors (each corresponding to a reduction in diameter of the core wire) in series with the parallel combination. Although use of a spring coil 16(1) is disclosed, it is to be understood that any resistive element or reactive element may be utilized to provide the adjustment as described with respect to the spring coil 16(1) above. The resistive and/or reactive components designed as part of the radiofrequency guidewire 10, such as the spring coil 16(1), may not only just serve to manipulate the heat dissipation on the radiofrequency guidewire 10 as exemplified above, but also to fulfil other purposes, such as optimizing the overall electrical performance of the guidewire system. For example, the spring coil 16(1), or another component designed on the radiofrequency guidewire 10, may be characteristically inductive to counteract the imaginary component in the radiofrequency ablation process, such as plasma discharge, thus by itself, or in part, serves as an impedance matching network. The facilitated impedance match can effectively enhance the power delivery efficiency by reducing the reflected power from the load back to the radiofrequency generator side due to impedance mismatching.

Figure 8:
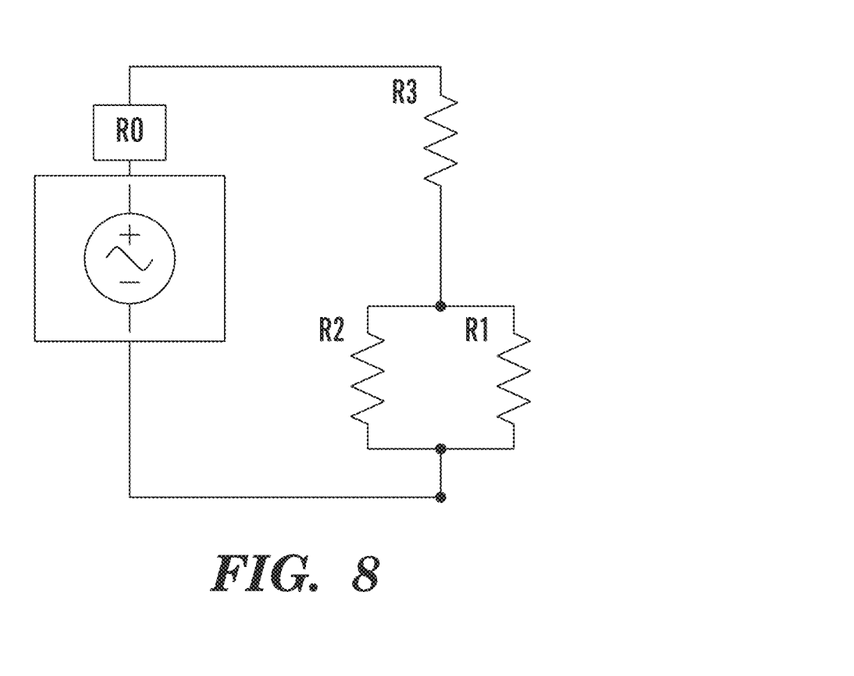
FIG. 8 is a simplified electrical schematic representing a radiofrequency generator and a radiofrequency guidewire of the present technology.

Referring again to FIG. 1, in another example, the radiofrequency generator may be adjusted to control plasma and heat conduction. By way of example only, by initially providing radiofrequency energy at a lower energy level, plasma initiation may be started at one location of the distal tip structure 20(1). By increasing the energy level, the plasma may be sustained, moved, or intensified to another location on the distal tip structure 20(1). Referring now to FIG. 8, the radiofrequency generator may consist of a power supply, and other functional components, such as a transformer, whose total output impedance seen by the output terminals of the generator is illustrated as R0. As an example, assuming R0 mainly represents the impedance of a transformer which is primarily designed to convert the low voltage output of the power supply to a high voltage to form plasma to aid in tissue ablation, the transformer may also participate in the system power dissipation such that R0 can be manipulated for the purpose of improving the power delivery and/or thermal condition on the distal end of the guidewire, e.g., by using a relatively large R0 in certain circumstances. Using this technique, it is possible to further reduce the voltage and power across resistor R1 to achieve lower temperature rise on R1.

Accordingly, with this technology, radiofrequency energy may be delivered to an occlusion for a more controlled generation of plasma. This provides for increased effectiveness of radiofrequency energy for ablating occlusions, as well as increased safety, including the use of lower voltage levels and lower energy levels. Additionally, the direction of energy away from the insulating material allows for the use of thinner, more flexible materials, providing better access to occlusions.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Accordingly, the invention is limited only by the following claims and equivalents thereto.

What is claimed is:

1. A radiofrequency guidewire comprising:
a core wire configured to be coupled to a radiofrequency generator, the core wire comprising a proximal end and a distal end with respect to the radiofrequency generator; and
a tip structure coupled to the core wire proximate the distal end, the tip structure comprising a semi-hemispherical base portion coupled to the distal end of the core wire and having a substantially rounded configuration and a tapered section extending from the semi-hemispherical base portion to a flat distal tip, wherein the tapered section has a reduced radius of curvature from the semi-hemispherical base portion, and extends from a first circumferential edge surface, provided by a first intersection between the outer circumference of the semi-hemispherical base portion and the tapered section, to a second circumferential edge surface, provided by a second intersection between the tapered section and an outer circumference of the flat distal tip, wherein the outer circumference of the semi-hemispherical base portion is greater than the outer circumference of the flat distal tip, wherein the first circumferential edge surface and the second circumferential edge surface each define an outer facing corner positioned to generate a higher electric field in a forward radial direction than other areas of the tip structure during a delivery of radiofrequency energy to the tip structure, with the outer facing corner of the second circumferential edge surface spaced within the outer facing corner of the first circumferential edge surface.

2. The radiofrequency guidewire as set forth in claim 1, wherein the second circumferential edge surface is located at an end of the tip structure located opposite the core wire.

3. The radiofrequency guidewire as set forth in claim 1, wherein the core wire comprises a proximal core wire section and a distal core wire section, wherein the distal core wire section comprises a smaller diameter than the proximal core wire section.

4. The radiofrequency guidewire as set forth in claim 1 further comprising an outer insulation layer extending along at least a portion of the length of the core wire.

5. The radiofrequency guidewire as set forth in claim 4, wherein the outer insulation layer comprises a dielectric material.

6. The radiofrequency guidewire as set forth in claim 4 further comprising a collar structure located proximate to the tip structure.

7. The radiofrequency guidewire as set forth in claim 6, wherein the collar structure is configured to provide insulation for the tip structure.

8. The radiofrequency guidewire as set forth in claim 6, wherein the collar structure comprises a material having a higher melting temperature than the outer insulation layer.

9. The radiofrequency guidewire as set forth in claim 6, wherein the collar structure encapsulates the tip structure within a dielectric barrier.

10. The radiofrequency guidewire as set forth in claim 6, wherein the collar structure is configured to impede propagation of vapor bubbles or shockwaves generated at the tip structure toward the core wire.

11. The radiofrequency guidewire as set forth in claim 10, wherein the collar structure has a substantially concave surface located proximate the tip structure.

12. The radiofrequency guidewire as set forth in claim 4 further comprising one or more resistive elements configured to create a parallel circuit for current sent from the radiofrequency generator through the core wire.

13. The radiofrequency guidewire as set forth in claim 4 further comprising a coil structure located along an inner surface of the outer insulation layer.

14. A method for treating a body region, the method comprising:
   delivering a guidewire to the body region, the guidewire comprising:
      a core wire configured to be coupled to a radiofrequency generator, the core wire comprising a proximal end and a distal end with respect to the radiofrequency generator; and
      a tip structure coupled to the core wire proximate the distal end, the tip structure comprising a semi-hemispherical base portion coupled to the distal end of the core wire and having a substantially rounded configuration and a tapered section extending from the semi-hemispherical base portion to a flat distal tip, wherein the tapered section has a reduced radius of curvature from the semi-hemispherical base portion, and extends from a first circumferential edge surface, provided by a first intersection between the outer circumference of the semi-hemispherical base portion and the tapered section, to a second circumferential edge surface, provided by a second intersection between the tapered section and an outer circumference of the flat distal tip, wherein the outer circumference of the semi-hemispherical base portion is greater than the outer circumference of the flat distal tip, wherein the first circumferential edge surface and the second circumferential edge surface each define an outer facing corner positioned to generate a higher electric field in a forward radial direction than other areas of the tip structure during a delivery of radiofrequency energy to the tip structure, with the outer facing corner of the second circumferential edge spaced within the outer facing corner of the first circumferential edge;
   positioning an opposing electrode proximate the tip structure;
   delivering radiofrequency energy through the guidewire from the radiofrequency generator, wherein an electrical field is generated proximate the tip structure with the electrical field strongest at the first and second circumferential edge surfaces to generate a plasma at the first and second circumferential edge surfaces to treat the body region.

15. The method as set forth in claim 14, wherein the second circumferential edge surface is located at an end of the tip structure located opposite the core wire.

16. The method as set forth in claim 14, wherein the first and second circumferential edge surfaces are located at opposing outer edges of the tip structure.

17. The method as set forth in claim 14, wherein the core wire comprises a proximal core wire section and a distal core wire section, wherein the distal core wire section comprises a smaller diameter than the proximal core wire section.

18. The method as set forth in claim 14, wherein the guidewire further comprises an outer insulation layer extending along at least a portion of the length of the core wire.

19. The method as set forth in claim 18, wherein the outer insulation layer comprises a dielectric material.

20. The method as set forth in claim 18, wherein the guidewire further comprises a collar structure located proximate to the tip structure.

21. The method as set forth in claim 20, wherein the collar structure is configured to provide insulation for the tip structure.

22. The method as set forth in claim 20, wherein the collar structure comprises a material with a higher melting temperature than the outer insulation layer.

23. The method as set forth in claim 20, wherein the collar structure encapsulates the tip structure within a dielectric barrier.

24. The method as set forth in claim 20, wherein the collar structure is configured to impede propagation of vapor bubbles or shockwaves generated at the tip structure toward the core wire.

25. The method as set forth in claim 24, wherein the collar structure has a substantially concave surface located proximate the tip structure.

26. The method as set forth in claim 18 further comprising one or more resistive elements configured to create a parallel circuit for current sent from the radiofrequency generator through the core wire.

27. The method as set forth in claim 18 further comprising a coil structure located along an inner surface of the outer layer.

28. The method as set forth in claim 14, wherein the opposing electrode is a second guidewire delivered to the body region in a same direction as the guidewire.

29. The method as set forth in claim 14, wherein the opposing electrode is a second guidewire delivered to the body region in an opposing direction to the guidewire.

30. The method as set forth in claim 14, wherein the opposing electrode is located on an area of a patient's skin.

31. The method as set forth in claim 14, wherein the body region is an occlusion in a blood vessel.

32. The method as set forth in claim 31, wherein the reduced radius of curvature of the tapered section is selected based on a type of the occlusion.

33. The method as set forth in claim 14 further comprising:
   adjusting the delivery of radiofrequency energy to alter the position of plasma generation on the tip structure.

34. The method as set forth in claim 14, wherein the body region is a duct.

35. The method as set forth in claim 14, wherein the body region is a tissue comprising a prostate gland, a tumor, or a cardiac tissue.

36. The method as set forth in claim 14 further comprising:
   increasing the total output impedance of the radiofrequency generator to lower the thermal condition in the distal section of the guidewire.

* * * * *